(12) United States Patent
Kuehl et al.

(10) Patent No.: US 11,404,259 B2
(45) Date of Patent: Aug. 2, 2022

(54) RELIABLE AND AUTOMATIC MASS SPECTRAL ANALYSIS

(71) Applicant: CERNO BIOSCIENCE LLC, Las Vegas, NV (US)

(72) Inventors: Don Kuehl, Windham, NH (US); Stacey Simonoff, Portsmouth, NH (US); Yongdong Wang, Las Vegas, NV (US)

(73) Assignee: CERNO BIOSCIENCE LLC, Las Vegas, NV (US)

( * ) Notice: Subject to any disclaimer, the term of this patent is extended or adjusted under 35 U.S.C. 154(b) by 156 days.

(21) Appl. No.: 16/971,229

(22) PCT Filed: Feb. 19, 2019

(86) PCT No.: PCT/US2019/018568
§ 371 (c)(1),
(2) Date: Aug. 19, 2020

(87) PCT Pub. No.: WO2019/161382
PCT Pub. Date: Aug. 22, 2019

(65) Prior Publication Data
US 2021/0098241 A1  Apr. 1, 2021

Related U.S. Application Data

(60) Provisional application No. 62/632,414, filed on Feb. 19, 2018.

(51) Int. Cl.
*H01J 49/00* (2006.01)
*G16B 40/00* (2019.01)
(Continued)

(52) U.S. Cl.
CPC .......... *H01J 49/0036* (2013.01); *G01N 30/72* (2013.01); *G01N 30/8631* (2013.01);
(Continued)

(58) Field of Classification Search
CPC . H01J 49/0036; G01N 30/72; G01N 30/8631; G01N 30/8644; G01N 30/8675; G01N 33/6848; G16B 40/00
See application file for complete search history.

(56) References Cited

U.S. PATENT DOCUMENTS 6,410,915 B1  6/2002  Bateman et al.
7,499,807 B1 * 3/2009  Tolmachev ......... H01J 49/0009
                                            702/182
(Continued)

FOREIGN PATENT DOCUMENTS

EP        2 399 123 A1   12/2011
EP        2594936 A2 *   5/2013  ......... G01N 30/8675
WO    2010/095941 A1    8/2010

OTHER PUBLICATIONS

Von Stokkum et al, "Global Analysis of Multiple Gas Chromatography-Mass Spectrometry (GC-MS) Data Sets: A Method for Resolution of Co-Eluting Components With Comparison to MCR-ALS", Chemometrics and Intelligent Laboratory Systems, Feb. 2009 (Year: 2009).*

(Continued)

*Primary Examiner* — David E Smith
(74) *Attorney, Agent, or Firm* — Ohlandt, Greeley, Ruggiero and Perle, LLP

(57) ABSTRACT

A method, mass spectrometer and computer readable medium for acquiring mass spectral data in raw profile; detecting presence of compounds and relevant time window; performing multivariate statistical analysis of raw profile data in a time window to determine compounds; obtaining separation time profiles for detected compounds containing respective time locations in a time window; and computing pure mass spectra for compounds based on separation time profiles or time locations. A method, mass spectrometer and computer readable medium for acquiring mass spectral data in raw profile of a known and unknown sample; combining mass spectral scans for a sample into a single mass spectrum across a separation time window; performing multivariate statistical analysis of the acquired mass spectral data and computing a distance measure between the known and (Continued)

unknown sample; and using the distance measure as an indication for an unknown sample belonging to a known sample or sample group.

43 Claims, 8 Drawing Sheets

(51) Int. Cl.
   *G01N 30/72* (2006.01)
   *G01N 30/86* (2006.01)
   *G01N 33/68* (2006.01)

(52) U.S. Cl.
   CPC ..... *G01N 30/8644* (2013.01); *G01N 30/8675* (2013.01); *G01N 33/6848* (2013.01); *G16B 40/00* (2019.02)

(56) References Cited

U.S. PATENT DOCUMENTS

| | | |
|---|---|---|
| 2004/0181351 A1 | 9/2004 | Thompson et al. |
| 2006/0169883 A1* | 8/2006 | Wang .................. H01J 49/0009 250/282 |
| 2006/0271310 A1 | 11/2006 | Ito |
| 2008/0052011 A1* | 2/2008 | Wang .................. H01J 49/0036 702/27 |
| 2009/0166522 A1 | 7/2009 | Umemura |
| 2009/0210167 A1 | 8/2009 | Wang |
| 2009/0294645 A1* | 12/2009 | Gorenstein ............ G16C 20/20 250/288 |
| 2010/0187414 A1 | 7/2010 | Gorenstein |

OTHER PUBLICATIONS

International Search Report dated May 6, 2019 from International Patent Application No. PCT/US2019/018568, 3 pages.
Written Opinion dated May 6, 2019 from International Patent Application No. PCT/US2019/018568, 7 pages.
International Preliminary Report on Patentability dated May Sep. 3, 2020 from International Patent Application No. PCT/US2019/018568, 5 pages.
Extended European Search Report dated Jan. 14, 2022 from corresponding European Patent Application No. 19754841.5, 13 pages.
Von Stokkum et al.; "Global Analysis of Multiple Gas Chromatography-mass Spectrometry (GC/MS) data sets: A Method for Resolution of Co-Eluting Components with Comparison to MCR-ALS"; Chemometrics and Intelligent Laboratory Systems, Elsevier Science Publishers B.V. Amsterdam, NL, vol. 95, No. 2, Feb. 15, 2009, pp. 150-163.

* cited by examiner

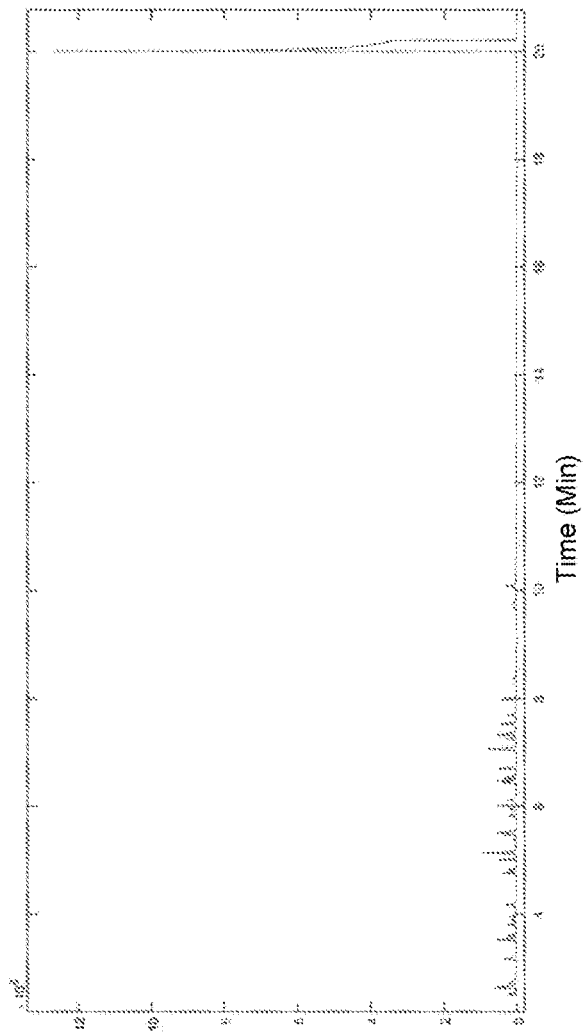

RELIABLE AND AUTOMATIC MASS SPECTRAL ANALYSIS

CROSS REFERENCE TO RELATED PATENT APPLICATIONS/PATENTS

U.S. Pat. Nos. 6,983,213, 7,493,225 and 7,577,538; International Patent Application PCT/US2004/013096, filed on Apr. 28, 2004; U.S. Pat. No. 7,348,553; International Patent Application PCT/US2005/039186, filed on Oct. 28, 2005; U.S. Pat. No. 8,010,306, International Patent Application PCT/US2006/013723, filed on Apr. 11, 2006; U.S. Pat. No. 7,781,729, International Patent Application PCT/US2007/069832, filed on May 28, 2007; and U.S. provisional patent application Ser. No. 60/941,656, filed on Jun. 2, 2007 and as International Patent Application PCT/US2008/065568 published as WO 2008/151153.

The entire teachings of these patent documents are hereby incorporated herein by reference, in their entireties, for all purposes.

FIELD OF THE INVENTION

The present invention generally relates to the field of Mass Spectrometry (MS) and, more particularly, to methods for acquiring, processing, and analyzing MS data.

BACKGROUND OF THE INVENTION

Mass Spectrometry (MS) is 100-year-old technology that relies on the ionization of molecules, the dispersion of the ions by their masses, and the proper detection of the ions on the appropriate detectors. There are many ways to achieve each of these three key MS processes which give rise to different types of MS instrumentations having distinct characteristics.

Many ionization techniques are available to ionize molecules entering MS system so that they can be properly charged before mass dispersion. These ionization schemes include Electrospray Ionization (ESI), Electron Impact Ionization (EI) through the impact of high-energy electrons, Chemical Ionization (CI) through the use of reactive compounds, and Matrix-Assisted Laser Desorption and Ionization (MALDI).

Once the molecules have been charged through ionization, each ion will have a corresponding mass-to-charge (m/z) ratio, which will become the basis to mass dispersion. Based on the physical principles used, there are many different ways to achieve mass dispersion and subsequent ion detection, resulting in mass spectral data similar in nature but different in details. A few of the commonly seen configurations include: magnetic/electric sector; quadrupoles; Time-Of-Flight (TOF); and Fourier Transform Ion-Cyclotron Resonance (FT ICR).

The sector MS configuration is the most straight-forward mass dispersion technique where ions with different m/z ratios would separate in an electric/magnetic field and exit this field at spatially separated locations where they will be detected with either a fixed array of detector elements or a movable set of small detectors that can be adjusted to detect different ions depending on the application. This is a simultaneous configuration where all ions from the sample are separated simultaneously in space rather than sequentially in time.

The quadrupoles configuration is perhaps the most common MS configuration where ions of different m/z values will be filtered out of a set of (usually 4) parallel rods through the manipulation of RF/DC ratios applied to these rod pairs. Only ions of a certain m/z value will survive the trip through these rods at a given RF/DC ratio, resulting in the sequential separation and detection of ions. Due to its sequential nature, only one detector element is required for detection. Another configuration that uses ion traps can be conceptually considered a special example of quadrupole MS.

The Time-Of-Flight (TOF) configuration is another sequential dispersion and detection scheme that lets ions enter through a high vacuum flight tube before detection. Ions of different m/z values would arrive at different times to the detector and the arrival time can be related to the m/z values through the use of known calibration standard(s).

In Fourier Transform Ion-Cyclotron Resonance (FT ICR), all ions can be introduced to an ion cyclotron where ions of different m/z ratios would be trapped and resonate at different frequencies. These ions can be pulsed out through the application of a Radio Frequency (RF) signal and the ion intensities measured as a function of time on a detector. Upon Fourier transformation of the time domain data measured, one gets back the frequency domain data where the frequency can be related back to m/z through the use of known calibration standard(s). Orbitrap MS systems can be conceptually considered as a special case of FT MS.

As discussed in the cross-referenced U.S. Pat. No. 6,983,213, a mass spectral data trace is typically subjected to peak analysis where peaks (ions) are identified. This peak detection routine is a highly empirical and compounded process where peak shoulders, noise in data trace, baselines due to chemical backgrounds or contamination, isotope peak interferences, etc., are considered. For the peaks identified, a process called centroiding is typically applied to report only two data values, m/z location and estimated peak area (or peak height), wherever an MS peak is detected. While highly efficient in terms of data storage, this is a process plagued by many adjustable parameters that can make an isotope appear or disappear with no objective measures of the centroiding quality, due to the many interfering factors mentioned above and the intrinsic difficulties in determining peak areas in the presence of other peaks and/or baselines. Unfortunately for many MS systems, especially quadrupole MS systems, this MS peak detection and centroiding are conventionally set up by default as part of the MS method to occur during data acquisition down at the firmware level, leading to irreparable damages to the MS data integrity, even for pure component mass spectral data in the absence of any spectral interferences from other co-existing compounds or analytes. As pointed out in U.S. Pat. No. 6,983,213, these damages or disadvantages include:

a. Lack of mass accuracy on the most commonly used unit mass resolution MS systems. The centroiding process forces the reported mass value into integer m/z with ±1 Da or other m/z values with at least ±0.1 Da mass error, whereas the properly calibrated raw profile mode MS data (without centroiding) using the method disclosed in U.S. Pat. No. 6,983,213 can be accurate to ±0.005 Da, a factor of approximately 100 improvement.

b. Large peak integration error. Centroiding without full mass spectral calibration including MS peak shape calibration suffers from uncertainty in mass spectral peak shape, its variability, the isotope peaks, the baseline and other background signals, the random noise, leading to both systematic and random errors for either strong or weak mass spectral peaks.

c. Large isotope abundance error. Separating the contributions from various closely located isotopes (e.g., A and A+1) on conventional MS systems with unit mass resolution either ignores the contributions from neighboring isotope peaks or over-estimates them, resulting in errors for dominating isotope peaks and large biases for weak isotope peaks or even complete elimination of the weaker isotopes.

d. Nonlinear operation. The centroiding typically uses a multi-stage disjointed process with many empirically adjustable parameters during each stage. Systematic errors (biases) are generated at each stage and propagated down to the later stages in an uncontrolled, unpredictable, and nonlinear manner, making it impossible for the algorithms to report meaningful statistics as measures of data processing quality and reliability.

e. Dominating systematic errors. In most of MS applications, ranging from industrial process control and environmental monitoring to protein identification or biomarker discovery, instrument sensitivity or detection limit has always been a focus and great efforts have been made in many instrument systems to minimize measurement error or noise contribution in the signal. Unfortunately, the typical centroiding process currently in use create a source of systematic error even larger than the random noise in the raw data, thus becoming the limiting factor in instrument sensitivity.

f. Mathematical and statistical inconsistency. The many empirical approaches currently used in centroiding make the whole processing inconsistent either mathematically or statistically. The peak processing results can change dramatically on slightly different data without any random noise or on the same synthetic data with slightly different noise. In order words, the results of the peak centroiding are not robust and can be unstable depending on a particular experiment or data acquisition.

g. Instrument-to-instrument or tune-to-tune variability. It has usually been difficult to directly compare raw mass spectral data from different MS instruments due to variations in the mechanical, electromagnetic, or environmental tolerances. With the typical centroiding applied to the actual raw profile mode MS data, it not only adds to the difficulty of quantitatively comparing results from different MS instruments due to the quantized nature of the centroiding process and centroid data, but also makes it difficult, if not impossible, to track down the source or possible cause of the variability once the MS data have been reduced to centroid data.

For a well separated analyte with pure mass spectrum and without any spectral interferences, MS centroiding is quite problematic as is due to the above listed reasons. For unresolved or otherwise co-eluting analytes or compounds in complex samples (e.g., petroleum products or essential oils) even after extensive chromatographic separation (e.g., 1-hr GC separation of essential oils or LC separation of biological samples with post translational modification such as deamidation), the above centroid processing problem would only be further aggravated due to the mutual mass spectral interferences present and the quantized nature of the MS centroids, which makes mass spectral data no longer linearly additive. This necessarily makes the MS centroid spectrum of a mixture different from the sum of MS centroids obtained from each individual pure spectrum, making the nonlinear and systematic centroiding error worse and even intractable. For this reason, the conventional co-elution deconvolution approach in common use, called AMDIS (Automated Mass Spectral Deconvolution & Identification System) as reported in "Optimization and Testing of Mass Spectral Library Search Algorithms for Compound Identification" Stein, S. E.; Scott, D. R. J. Amer. Soc. Mass Spectrom. 1994, 5, 859-866, which typically operates with MS centroid data, often fails to determine the correct number of co-elution compounds, derive the correct separation time profiles (called chromatograms in the case of chromatographic separation) of individual compounds or analytes, or compute the correct pure component/analyte mass spectra for reliable library (e.g., NIST EI MS library) search and compound identification.

For complex samples without any time-based (e.g., chromatographic) separation due to the need for speedy analysis or detection, using, as an example, novel ionization techniques such as DART (Direct Analysis in Real Time), reported in R. B. Cody; J. A. Laramée; H. D. Durst (2005) "Versatile New Ion Source for the Analysis of Materials in Open Air under Ambient Conditions". Anal. Chem. 77 (8): 2297-2302, the mass spectrum may become so complex that there may not be visually separable mass spectral peaks for either detection or centroiding, leading possibly to the outright total failure of conventional mass spectral data acquisition, processing, and analysis.

Accordingly, it would be desirable and highly advantageous to have methods to avoid MS peak detection and centroiding altogether that overcome the above-described deficiencies and disadvantages of the prior art.

SUMMARY OF THE INVENTION

The present application is directed to the following improvements:

1. An accurate approach for the determination of independent analytes contained in a chromatographic peak, through multivariate statistical analysis such as the principal component analysis (PCA) of corresponding profile mode mass spectral data acquired in a relevant separation time window. It's critical to use profile mode mass spectral data, instead of the centroid data currently in use.

2. An accurate approach to completely model the underlying chromatographic peak shape functions involved, through the use of a set of chromatographic standards. Reference is made to U.S. Pat. Nos. 6,983,213 and 7,493,225.

3. With the chromatographic peak shape fully defined, only the peak (e.g., center) positions of the involved independent analytes need to be determined to fully define and resolve the mutually overlapping components hidden inside a chromatographic peak, e.g., through Simplex optimization with initial peak positions through iterative improvements and multiple linear regression (MLR).

4. With each chromatographic peak well defined, it is feasible to compute the pure mass spectrum for each analyte for either qualitative identification (e.g., through NIST library search) or quantitative analysis through multiple linear regression. Reference is made to U.S. Pat. No. 7,577,538.

5. Application of accurate mass and spectral accuracy analysis to confirm the molecular ion or its fragment ions to increase the identification confidence of a compound already known in a library (e.g., NIST library) or to aid in the elucidation of an unknown or new compound not contained in a library.

6. Additional identification confidence may also be gained through the use of retention indexes available for compounds already contained in a compound library (e.g., NIST library).

7. An approach to combine multiple mass spectral scans acquired over a given separation time window and compare among similar or different samples for the purpose of differentiating one sample from another, for the purpose of sample or product-type analysis.

Each of these aspects will be described below along with experimental results to demonstrate their utilities.

BRIEF DESCRIPTION OF THE DRAWINGS

FIG. 2A and FIG. 2B are two graphs of a typical TIC (Total Ion Chromatogram) from a GC/MS run of a semi-volatile organic compound sample, where the bottom graph is a zoomed-in version of the top graph

A component or a feature that is common to more than one drawing is indicated with the same reference number in each of the drawings.

DETAILED DESCRIPTION OF THE PREFERRED EMBODIMENTS

Figure 1:
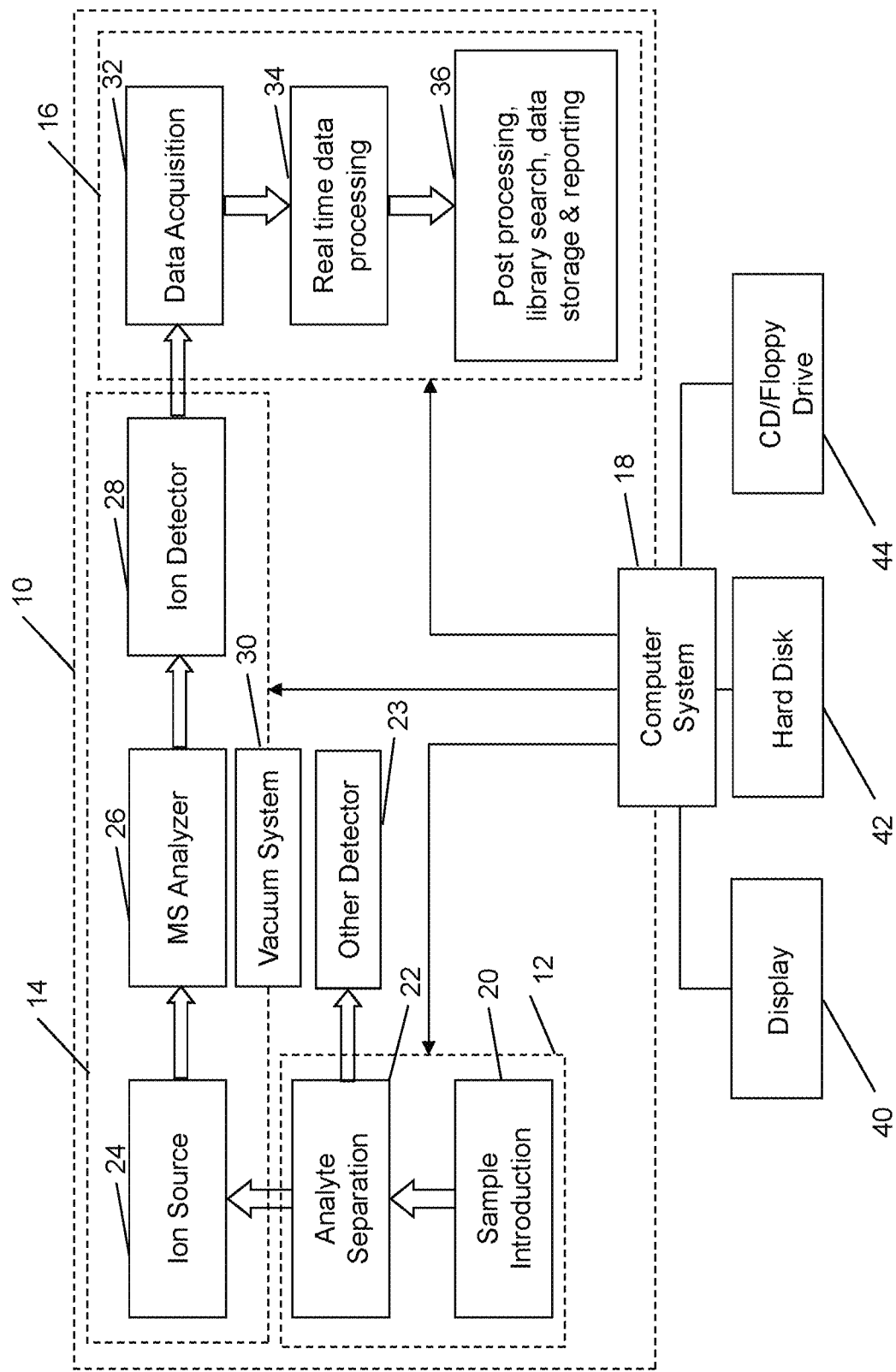
FIG. 1 is a block diagram of a mass spectrometer system that can utilize the methods disclosed herein.

Referring to FIG. 1, there is shown a block diagram of an analysis system 10, that may be used to analyze proteins or other molecules, as noted above, incorporating features of the present invention. Although the present invention will be described with reference to the single embodiment shown in the drawings, it should be understood that the present invention can be embodied in many alternate forms of embodiments. In addition, any suitable types of components could be used.

Analysis system 10 has a sample preparation portion 12, other detector portion 23, a mass spectrometer portion 14, a data analysis system 16, and a computer system 18. The sample preparation portion 12 may include a sample introduction unit 20, of the type that introduces a sample containing proteins, peptides, or small molecule drug of interest to system 10, such as LCQ Deca XP Max, manufactured by Thermo Fisher Scientific Corporation of Waltham, Mass., USA. The sample preparation portion 12 may also include an analyte separation unit 22, which is used to perform a preliminary separation of analytes, such as the proteins to be analyzed by system 10. Analyte separation unit 22 may be any one of a chromatography column, an electrophoresis separation unit, such as a gel-based separation unit manufactured by Bio-Rad Laboratories, Inc. of Hercules, Calif., or other separation apparatus such as ion mobility or pyrolysis etc. as is well known in the art. In electrophoresis, a voltage is applied to the unit to cause the proteins to be separated as a function of one or more variables, such as migration speed through a capillary tube, isoelectric focusing point (Hannesh, S. M., Electrophoresis 21, 1202-1209 (2000), or by mass (one dimensional separation)) or by more than one of these variables such as by isoelectric focusing and by mass. An example of the latter is known as two-dimensional electrophoresis.

The mass spectrometer portion 14 may be a conventional mass spectrometer and may be any one available, but is preferably one of TOF, quadrupole MS, ion trap MS, qTOF, TOF/TOF, or FTMS. If it has an electrospray ionization (ESI) ion source, such ion source may also provide for sample input to the mass spectrometer portion 14. In general, mass spectrometer portion 14 may include an ion source 24, a mass analyzer 26 for separating ions generated by ion source 24 by mass to charge ratio, an ion detector portion 28 for detecting the ions from mass analyzer 26, and a vacuum system 30 for maintaining a sufficient vacuum for mass spectrometer portion 14 to operate most effectively. If mass spectrometer portion 14 is an ion mobility spectrometer, generally no vacuum system is needed and the data generated are typically called a plasmagram instead of a mass spectrum.

In parallel to the mass spectrometer portion 14, there may be other detector portion 23, where a portion of the flow is diverted to for nearly parallel detection of the sample in a split flow arrangement. This other detector portion 23 may be a single channel UV detector, a multi-channel UV spectrometer, or Reflective Index (RI) detector, light scattering detector, radioactivity monitor (RAM) etc. RAM is most widely used in drug metabolism research for 14C-labeled experiments where the various metabolites can be traced in near real time and correlated to the mass spectral scans.

The data analysis system 16 includes a data acquisition portion 32, which may include one or a series of analog to digital converters (not shown) for converting signals from ion detector portion 28 into digital data. This digital data is provided to a real time data processing portion 34, which processes the digital data through operations such as summing and/or averaging. A post processing portion 36 may be used to do additional processing of the data from real time data processing portion 34, including library searches, data storage and data reporting.

Computer system 18 provides control of sample preparation portion 12, mass spectrometer portion 14, other detector portion 23, and data analysis system 16, in the manner described below. Computer system 18 may have a conventional computer monitor or display 40 to allow for the entry of data on appropriate screen displays, and for the display of the results of the analyses performed. Computer system 18 may be based on any appropriate personal computer, operating for example with a Windows® or UNIX® operating system, or any other appropriate operating system. Computer system 18 will typically have a hard drive 42 or other type of data storage medium, on which the operating system and the program for performing the data analysis described below, is stored. A removable data storage device 44 for accepting a CD, floppy disk, memory stick or other data storage medium is used to load the program in accordance with the invention on to computer system 18. The program for controlling sample preparation portion 12 and mass spectrometer portion 14 will typically be downloaded as firmware for these portions of system 10. Data analysis system 16 may be a program written to implement the processing steps discussed below, in any of several programming languages such as C++, JAVA or Visual Basic.

Figure 3A:
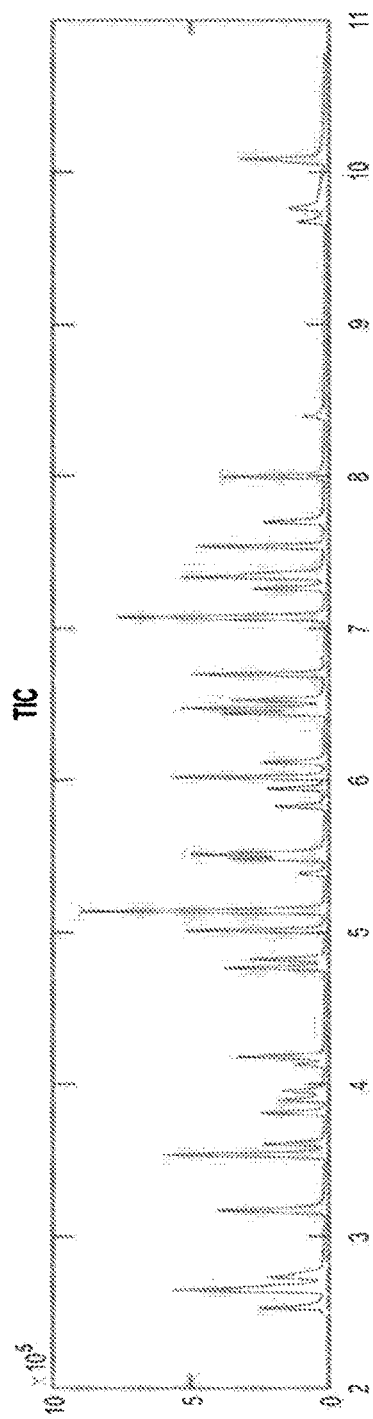
FIG. 3A, FIG. 3B and FIG. 3C are three graphs of the analysis results where the top graph (A) is the original TIC, the middle graph (B) indicates the t-values of the detected chromatographic peaks, and the bottom graph (C) indicates the number of analytes determined under each detected peak
Figure 3B:
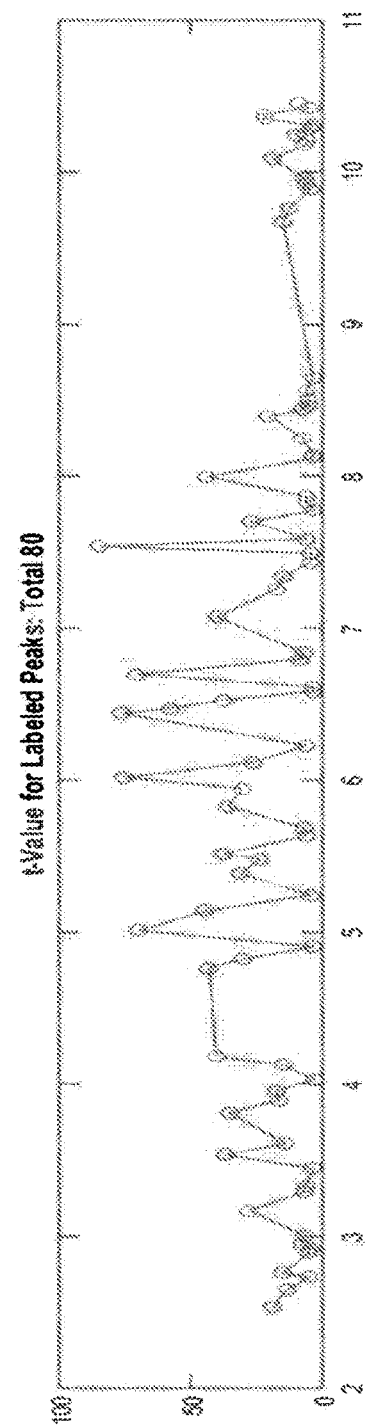
Figure 3C:
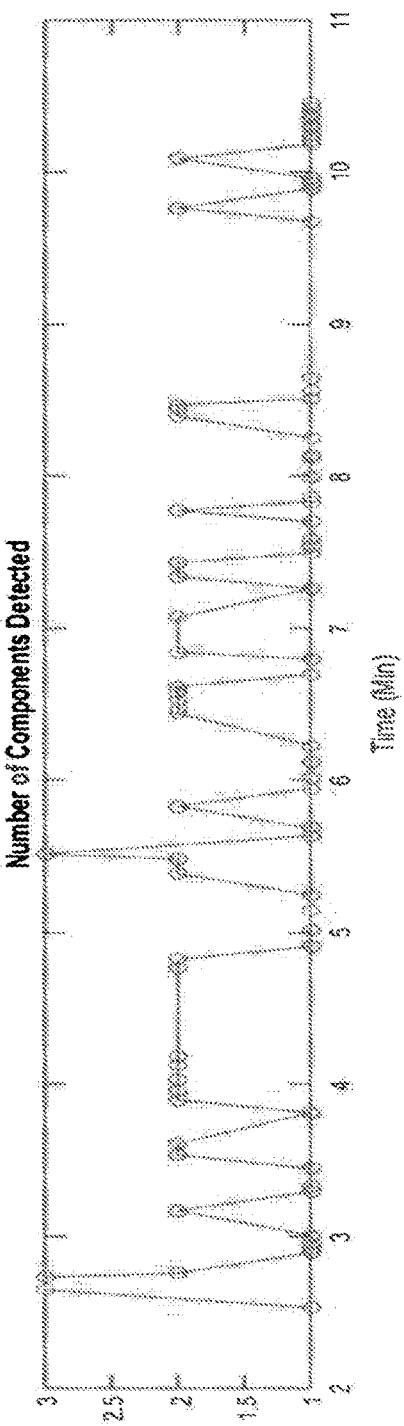
Figure 4B:
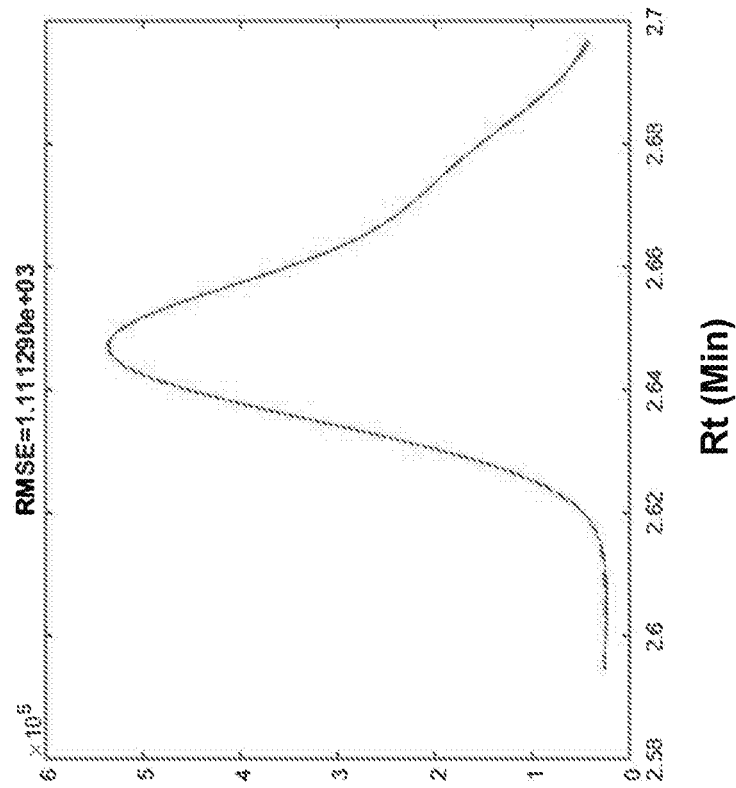
FIG. 4A and FIG. 4B are two graphs of the deconvoluted (A) and reproduced TIC (B) for each of the analytes under a 3-component mixture peak with flat baseline
Figure 4A:
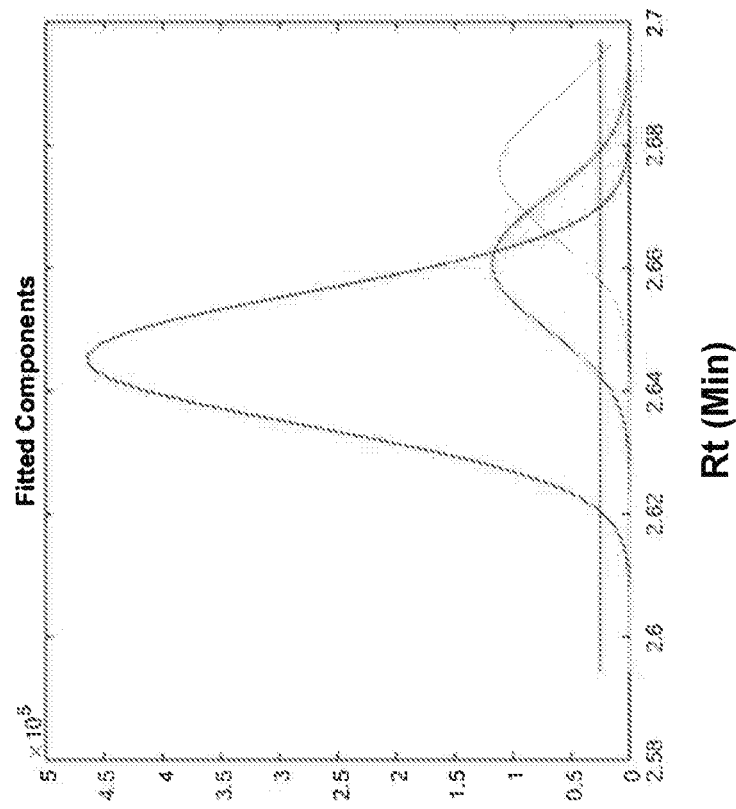
Figure 5A:
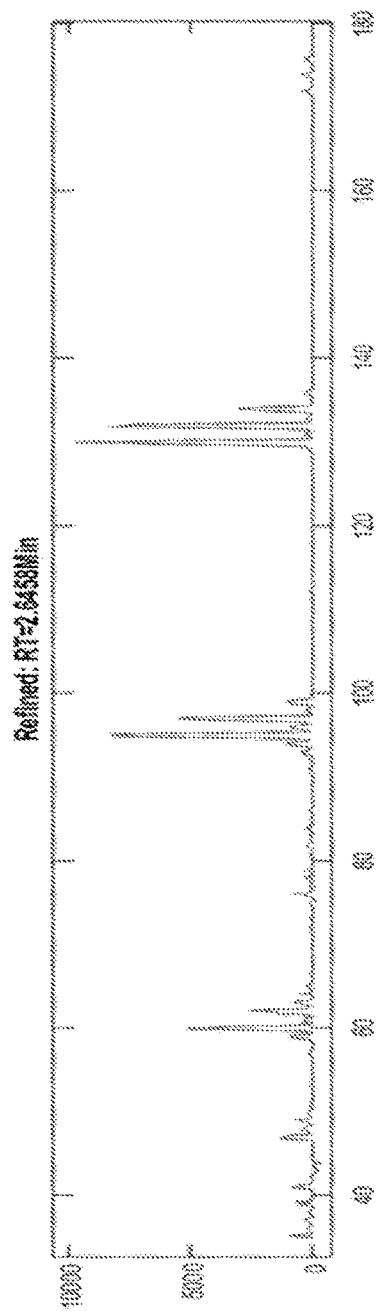
FIG. 5A, FIG. 5B and FIG. 5C are the graphs of the three deconvoluted pure analyte mass spectra corresponding to the three analytes shown in FIG. 4.
Figure 5B:
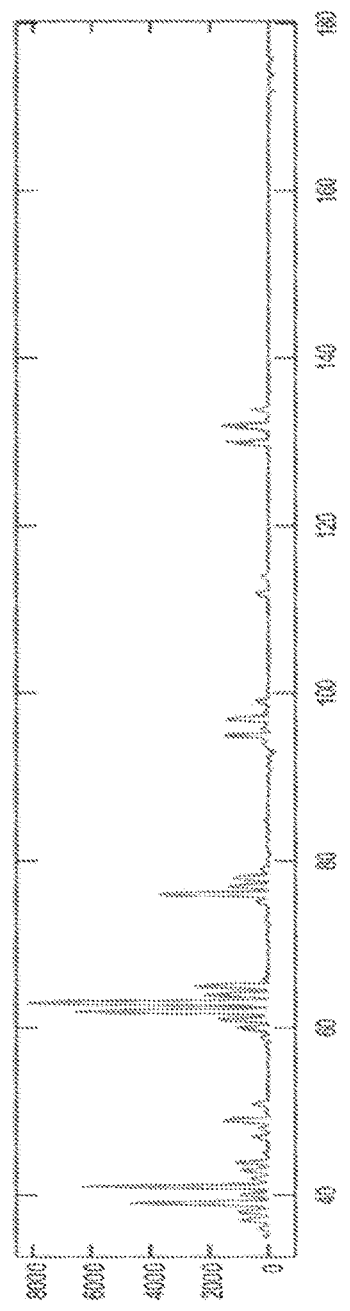
Figure 5C:
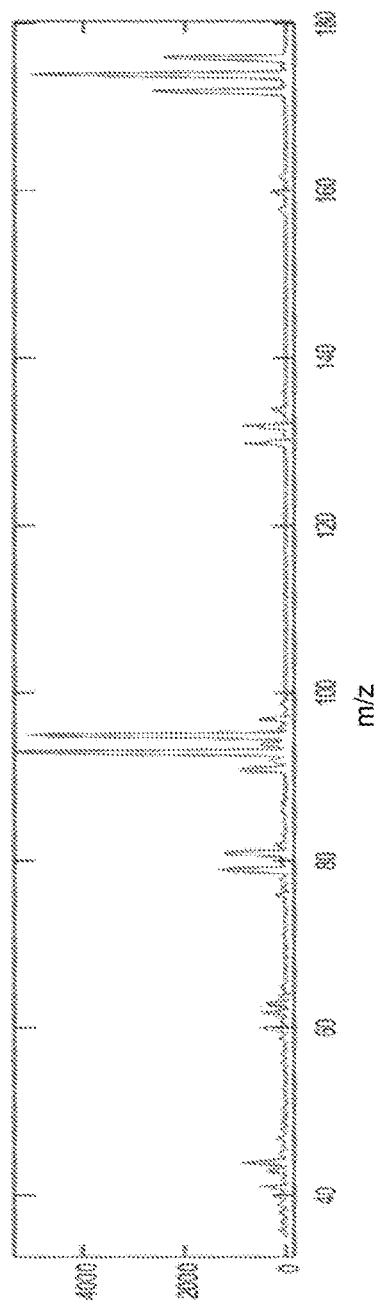

In the preferred embodiment of this invention, a sample is acquired through the chromatography/mass spectrometry system described in FIG. 1 with mass spectral profile mode raw data continuously acquired throughout the run, resulting in a data run such as the one shown in FIG. 2, which is an example GC/MS run containing many chromatographic peaks, including PFTBA tune gas which can be used to perform the mass accuracy and spectral accuracy calibration to the raw profile mode mass spectral data before subsequent processing and analysis, using the approach described in the U.S. Pat. No. 6,983,213. The detailed steps involved in the subsequent processing and analysis would now be described:

a. Detection of all the chromatographic peaks from the TIC shown in in FIG. 2. This can be best accomplished with known pure chromatographic peak shape functions across the whole separation time range, which can be measured under the same chromatographic separation conditions using a set of known standards such as alkane with different carbon numbers to cover the required retention time range. One may also perform a chromatographic peak shape calibration to convert the actual peak shape into target peak shape, much like how mass spectral peak shape calibration is performed in U.S. Pat. No. 6,983,213 and further disclosed in the U.S. patent application Ser. No. 11/402,238, filed on Apr. 10, 2006. Once the chromatographic peak shape is well defined through either actual measurement or calibration, the peak detection and analysis method from U.S. Pat. No. 6,983,213 can be utilized to detect all chromatographic peaks in a chromatogram such as the one shown in FIG. 2B, with the peak detection results shown in FIG. 3.

b. FIG. 3B shows the t-value from the peak detection, which is a statistical indication for the statistical significance of the detected peak, where a t-value of 2.0 typically corresponds to about 95% confidence and a t-value of 3.0 for 99% confidence. Some of the detected peaks are pure and therefore ready for library search (identification) or quantitative analysis but some of which are not pure and would not be suitable for either. It is critical to identify these chromatographic peaks to assess their purity and ideally separate out the mutual interferences where there are impurities or co-eluting analytes. In order to achieve purity detection as well as the reliable deconvolution in the case of impurity or co-elution, it is imperative to have a reliable approach for the determination of independent analytes contained in a chromatographic peak or separation time window. This is accomplished by performing multivariate statistical analysis on the acquired profile mode mass spectral scan data (either raw or PFTBA calibrated) corresponding to the separation time window. The multivariate statistical analysis can be accomplished using a variety of well established algorithms known in the art, such as Principal Component Analysis (PCA) or Partial Least Squares, based on either Singular Value Decomposition or NIPALS algorithm (S. Wold, P. Geladi, K. Esbensen, J. Ohman, J. Chemometrics, 1987, 1(1), 41). FIG. 3C shows the number of independent components (analytes) determined for each significant chromatographic peak detected.

c. Once the correct number of components are determined, the next step is to deconvolute these given number of components from the mixture (of overlapping components) using the same profile mode mass spectral data in raw acquired form, or preferably in the PFTBA calibrated form for later more accurate compound identification (in addition to the advantage of better signal to noise due to the effect of applying the MS calibration filters).

d. With the chromatographic peak shape fully defined, only the peak (e.g., center) positions of the involved independent analytes or components need to be determined to fully define and resolve the overlapping components hidden inside a chromatographic peak, e.g., through Simplex optimization. For the 3-component mixture detected at Rt approximately 2.66 min shown in FIG. 4A, the three underlying and overlapping chromatographic peaks can be determined through a Simplex search, starting with a set of initial values which get refined iteratively with fitting residual from multiple linear regression (MLR) as objective function, using the method disclosed in U.S. Pat. No. 6,983,213 and further disclosed in the U.S. patent application Ser. No. 11/402,238, with the results as shown in FIG. 4A, which also includes a flat baseline. Other types of baseline beyond a flat baseline could also be accommodated. FIG. 4B indicates an excellent fit to the actual TIC using these components/analytes with their respective separation time profiles determined and shown in FIG. 4A.

e. Deconvolute the mixture mass spectral data into each pure mass spectrum for each analyte. With the deconvoluted pure chromatograms from FIG. 4A, it is possible to compute the corresponding pure mass spectrum for each individual analyte, as shown in FIG. 5A, FIG. 5B and FIG. 5C, through multiple linear regression (MLR) using the methodology referenced in U.S. Pat. Nos. 7,577,538 and 6,983,213.

f. The deconvoluted pure mass spectra are then used for either qualitative identification (e.g., NIST library search) or quantitative analysis by using the spectral intensities or by calibration through a series of concentration standards. Likewise, one may use the deconvoluted separation time profile for qualitative analysis and identification of compounds of interest, such as explosives detection using ion mobility or plasmagram, based on the fact that different explosive compounds have different and distinctive drift times. The separation time profile could also be used for quantitative analysis by using the profile intensities or through a series of concentration standards. In the case of GC/MS or LC/MS, one may normalize both the de-convoluted time profiles and the pure mass spectra and leave their quantitative information in a form of scaling factors for later quantitative analysis.

g. In the preferred embodiment with PFTBA tune gas turned on during a sample run (FIG. 2A), there is the added advantage for the application of accurate mass and spectral accuracy analysis to analyze both the molecular ion and fragment ions from EI MS. GC/MS is a powerful tool for the identification of both target and unknown compounds (compound ID). The basis for the technique relies upon the fact that when the eluting molecules are ionized via electron impact (EI) the relatively energetic source fragments the molecule in a way that provides a characteristic pattern which is indicative of the molecular structure. The pattern, both the fragments and relative abundance of the molecule, are searched against a library of measured spectra acquired at nominal mass resolution and ranked based on simple matching algorithms. The technique works quite well provided 1) the compound is pure (no background or coelution) and 2) the compound is in the library. In addition, the search results are not always fully definitive, and it would be valuable to have additional, orthogonal measurements to confirm the molecular identity. The CLIPS (Calibrated Line-shape Isotope Profile Search) search (reference is made to International Patent Application PCT/US2005/039186, filed on Oct. 28, 2005.) combines accurate mass and spectral accuracy to transform these robust, low resolution MS instruments into powerful tools for assisting in validating library search results or by providing additional information (the formula ID) of the molecular ion (the un-fragmented molecule) if available. It is important to distinguish between compound identification (ID) (the determination of the molecular structure) and formula ID (the determination of the molecular formula). The usual approach is to select the molecular ion and perform a CLIPS search to provide a formula ID that can be compared to the NIST search for validation, or, if a true unknown not in library, to provide a formula ID to provide initial insight into what the compound is. However, it would also be possible to do formula ID on the molecular ion as well as all the fragments. This can be very powerful for making a "guess" at the structure and is currently done by a handful of "experts" (who are a dying breed, much like in IR spectral interpretation experts) using only the nominal mass values. This can be done because there are a number of commonly produced fragments that can be deduced from the molecular ion simply by measuring the mass difference. But it is an art at best, and one that requires considerable skill. It would be highly desirable, and valuable, to be able to automatically and accurately determine all of the ion fragment formula IDs and perhaps even propose some possible compound IDs. This can be done using a series of CLIPS searches on all the ion fragments and then cross comparing the results. Any ion fragment must be a subset of the molecular ion, so all the fragments must be related, and hence there is a powerful constraint to take advantage of in automated spectral interpretation. One possible series of steps that could produce this information is set forth below.

i. Measure the average, calibrated profile spectrum over a chromatographic peak
ii. Locate all the monoisotopic peaks through peak detection
iii. Perform a CLIPS search on each ion fragment with accurate mass reported
iv. Cross-compare the CLIPS search hit lists using spectral accuracy (hereinafter "SA"), as disclosed in International Patent Application PCT/US2005/039186, filed on Oct. 28, 2005
v. If the SA of the fragment is above 90%, and is a subset of the molecular ion, the correct formula of the fragment has been identified
vi. If the SA of the fragment is above 90% but it is NOT a subset of the molecular ion, it may come from a different compound (mixture) and one may search the above hit lists for the next candidate compound and check its fragments
vii. If the SA of the fragment is below 90%, it is likely that the fragment is not spectrally pure and therefore suffers from the interference from the fragment ion of a different compound. If this is the case, examine the other fragments and determine whether they might be related to a second compound. In the end, one or more sets of fragmentations are determined. Unlike the MS "expert", the SA accurately confirms the formula ID of the fragments. If a mixture is discovered, logical fragments are proposed, and CLIPS searches to connect the related fragments are performed to provide the correct answer when the SA is above 90%. One common problem with impure fragments is a tendency to have the fragment but also the fragment—H, and these ions overlap. This is easily handled in the CLIPS search which can be expanded to include multiple ions for analysis.
viii. Providing the fragment formula IDs and mixture deconvolution in an automated fashion is very valuable. However, it may be possible to use commercial databases of chemical compounds (e.g. ChemSpider, a commercially available database) which have millions of compounds and using formula ID and some fragmentation rules to actually propose the structure ab initio.
ix. If the molecular ion is not present (which is not uncommon), the procedure can be utilized in reverse. For example, there are lists of common fragments available leading to structural clues. One can start with the simple case (pure, molecular ion available) and then add complexity to figure the best approach for each case. With many known compounds run at different chromatographic resolutions, unresolved mixtures can be created and examined in a controlled manner.

Figure 7:
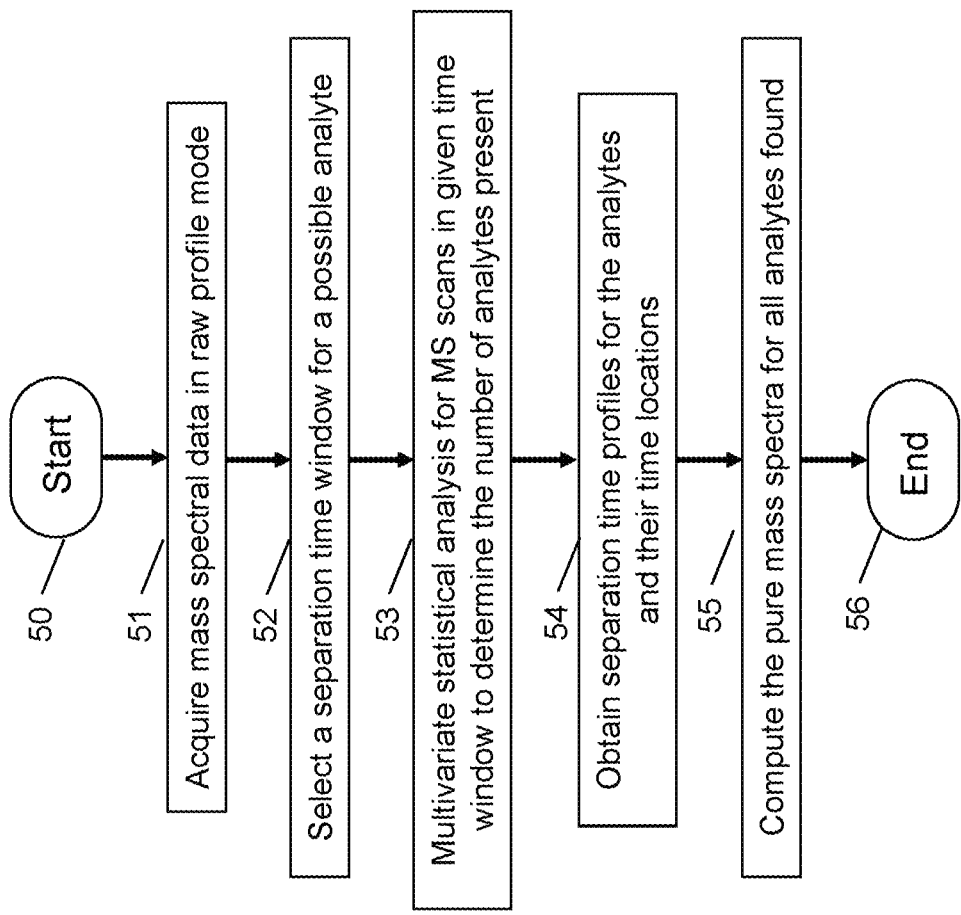
FIG. 7 includes a flow chart of one embodiment disclosed herein.

FIG. 7 shows the above steps in a flow chart of the first embodiment described herein where at 51, mass spectral data is acquired in raw profile mode. At 52 a time window is selected corresponding to a detected peak from above step (a) so as to avoid analyzing a separation time window where no possible compounds are found. On the other hand, when computing power is not a concern, especially with modern computers, one may opt to segment a whole run into a series of time windows arranged one right after another to cover the whole separation time range, or to compute the whole separate time range as a single time window. At 53, multivariate statistical analysis for MS scans in a given time window is performed to determine the number of analytes present. At 54, separation time profiles for the analytes and their time locations are obtained. At 55, the pure mass spectra for all analytes found are computed.

Figure 6:
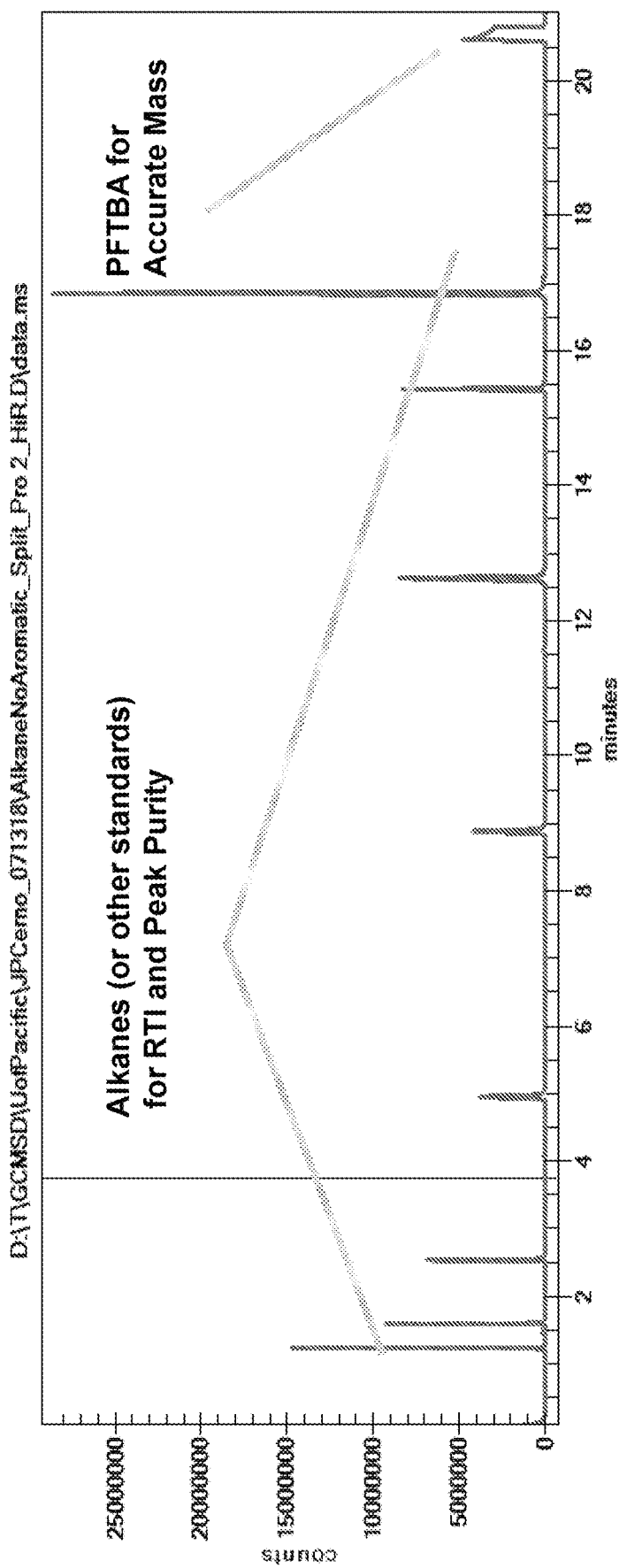
FIG. 6 includes the Total Ion Chromatogram (TIC) of a standard GC/MS run containing alkane retention time standards covering the retention time of interest and a PFTBA (Perfluorotributylamine) MS tune gas at the end of the run for mass accuracy and spectral accuracy calibration referenced in U.S. Pat. No. 6,983,213.

In the above preferred embodiment, the chromatographic time profile calibration standards such as alkane with different carbon numbers could also serve as a retention time standard for the conversion of actual retention time into retention index, which would allow for an additional dimension of compound identification by library search, since one could verify that the retention index calculated for an unknown compound also matches that of the library compound, in addition to a high library search score and high mass accuracy and spectral accuracy (SA). In fact, one could combine all these match scores to obtain an overall measurement of the match quality for compound identification. FIG. 6 shows a comprehensive standard run containing both the alkane calibration standard for chromatogram peak shape (separation time profile) and retention time and the PFTBA MS calibration standard, all inclusive in a single external run.

Additional advantage of chromatographic retention index search or match is for the user to determine a set or range of possible compounds from a known compound library based on the retention index as computed for a chromatographic peak and its associated confidence interval (or error bound). This set or range of tentatively identified compounds may be completely overlapped with each other with little or no time separation, making reliable deconvolution statistically unstable or mathematically impossible. One may in this case perform a regression analysis described in U.S. Pat. No. 7,577,538 between the measured profile mode mass spectrum and those constructed from a library for both qualitative analysis (identification) and quantitative analysis, using the regression coefficients as an indication of likely quantities and fitting statistics (e.g., t-values) as indication of the likely presence of compounds.

In many MS instruments such as quadrupole MS, the mass spectral scan time is not negligible compared to the compound (volatile compound, protein or peptide) elution time. Therefore, a significant skew would exist where the ions measured in one mass spectral scan comes from different time points during the LC elution, similar to what has been reported for GC/MS (Stein, S. E. et al, J. Am. Soc. Mass Spectrom. 5, 859 (1994)). It is preferred to correct for any time skew existing in a typical slow-scanning quadrupole chromatography/mass spectrometry system so as to make sure all masses are "acquired" at the same chromatographic retention time, regardless of scan rate or the actual time it takes to scan the designated mass range. This can be accomplished through interpolation of the actual acquisition time for each m/z location onto a grid of the same actual retention time, by taking into consideration of the MS scan rate, scan direction (from low to high m/z, vice versa, or a combination) and the dwell time in between two successive scans. This skew correction will improve the performance of multivariate statistical analysis such as multiple linear regression (MLR), Principal Component Analysis (PCA), Partial Least Squares (PLS) etc. for the determination of the correct number of components using mass spectral scans within a separation time window or deconvolution analysis.

For some MS applications, the sample may be too complex to be separated well enough even with the most elaborate separation method including 2D GC or LC separation, or the need for speedy onsite analysis dictates a faster separation or no separation at all. In this case, one may either obtain a single complicated mass spectrum for a sample without any separation (which would be fast but would suffer from ion suppression), such as the case typically with DART ion source, or one may simply sum or average mass spectral scans in profile mode in a given separation time window within a chromatographic run (which would not be as fast as direct analysis without separation but would suffer less from ion suppression due to some separation). While the complexity of the mass spectrum may not allow one to analyze and break down the resulting mass spectrum into individual compounds, one may be able to analyze these profile mode mass spectra and the corresponding samples (e.g., petroleum or essential oils) based on the complex mass spectral patterns as they are, through the use of multivariate statistical analysis such as PCA or PLS, to come up with statistical distance measurement between a known sample and an unknown sample to indicate their similarity or decide if one test/unknown sample belongs to a given product or sample group.

Figure 8:
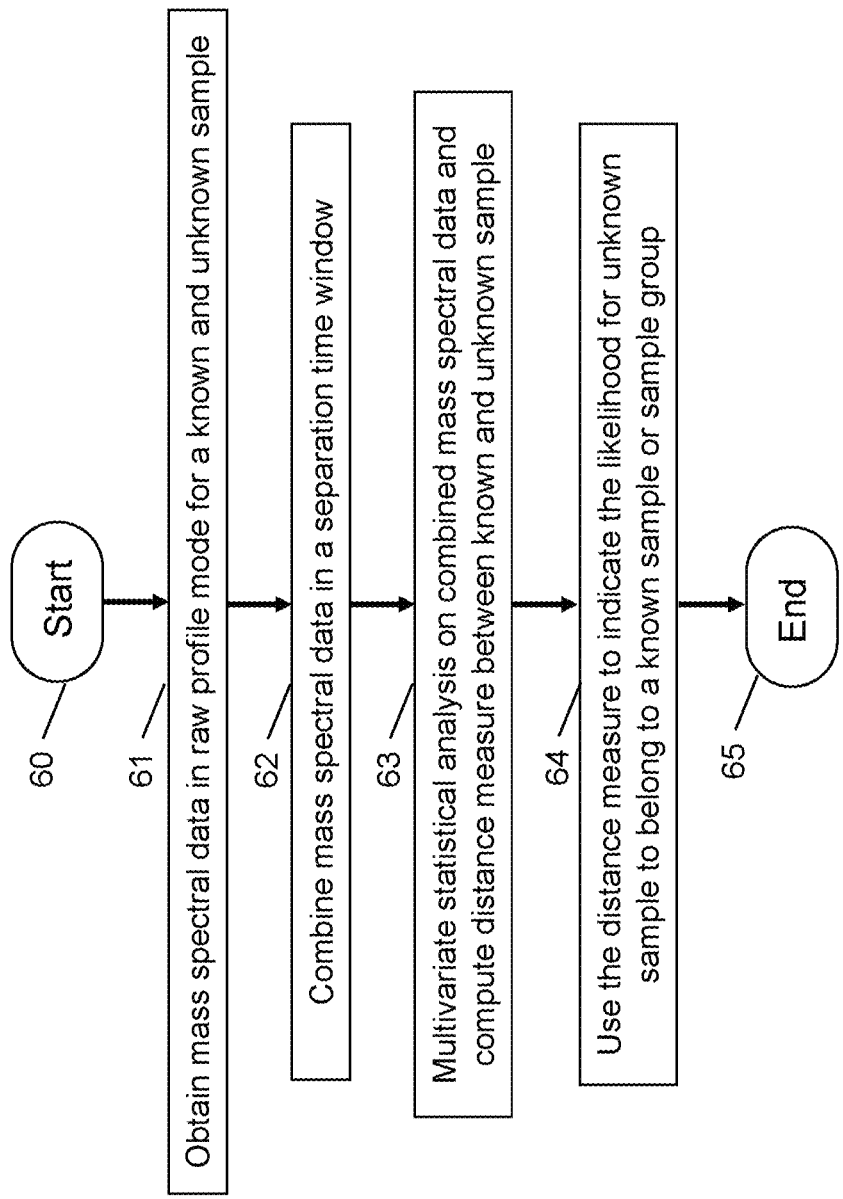
FIG. 8 includes a flow chart of another embodiment disclosed herein.

FIG. 8 shows a flow chart including the steps described above. At 61, mass spectral data in raw profile mode for a known and unknown sample is obtained. At 62, mass spectral data is combined in a separation time window. At 63, multivariate statistical analysis on combined mass spectral data is performed and a distance measure between known and unknown sample is computed. At 64, the distance is used as a measure to indicate the likelihood for unknown sample to belonging to a known sample or sample group.

Examples applications for this technique include airport security check for explosives, essential oil supplier quality control or assurance to detect and/or prevent possible adulteration or mis-labeling, petroleum product analysis and differentiation. In these cases, it would typically require a sample or sample group be acquired more than once so as to establish the statistical threshold above which one could be more sure of the actual difference between samples, above and beyond random statistical variations from the sample preparation or measurement process, or the expected batch-to-batch fluctuations in a production process. One may also create a collection of known samples and store them into a library of known samples with their associated mass spectra, into which new sample belonging to an existing sample group or a new sample group could be created and added to have a living and growing collection of samples and sample types, to be obtained or retrieved for future testing purposes or as a commercial product to be sold to other users. In this case, it is highly preferable to have the mass spectral profile mode data calibrated for both mass and spectral accuracy according to the method in U.S. Pat. No. 6,983,213 so that all mass spectral data and samples entered into the library will have the same consistent MS peak shape with accurate mass, regardless of the MS instruments or operating conditions (including tunes) used, to achieve the optimal analysis accuracy while saving time and efforts for the analysis.

Although the description above contains many specifics, these should not be construed as limiting the scope of the invention but as merely providing illustrations of some feasible embodiments of this invention.

Thus the scope of the disclosure should be determined by the appended claims and their legal equivalents, rather than by the examples given. Although the present disclosure has been described with reference to the embodiments described, it should be understood that it can be embodied in many alternate forms of embodiments. In addition, any suitable size, shape or type of elements or materials could be used. Accordingly, the present description is intended to embrace all such alternatives, modifications and variances which fall within the scope of the appended claims.

It will be understood that the disclosure may be embodied in a computer readable non-transitory storage medium storing instructions of a computer program which when executed by a computer system results in performance of steps of the method described herein. Such storage media may include any of those mentioned in the description above.

The techniques described herein are exemplary, and should not be construed as implying any particular limitation on the present disclosure. It should be understood that various alternatives, combinations and modifications could be devised by those skilled in the art. For example, steps associated with the processes described herein can be performed in any order, unless otherwise specified or dictated by the steps themselves. The present disclosure is intended to embrace all such alternatives, modifications and variances that fall within the scope of the appended claims.

The terms "comprises" or "comprising" are to be interpreted as specifying the presence of the stated features, integers, steps or components, but not precluding the presence of one or more other features, integers, steps or components or groups thereof.

What is claimed is:

1. A method for the analysis of compounds of interest through separation over time combined with detection by a mass spectrometer, comprising the steps of
   a. acquiring mass spectral data in a raw profile mode;
   b. selecting a relevant time window for presence of possible compounds of interest;
   c. performing multivariate statistical analysis of mass spectral raw profile mode data in a relevant time window to determine the number of compounds present;
   d. obtaining separation time profiles for detected compounds of interest and their respective time locations in the relevant time window; and
   e. computing a pure mass spectra for all compounds of interest corresponding to their respective separation time profiles or time locations.

2. The method of claim 1, where the technique for separation is one of gas chromatography (GC/MS), liquid chromatography (LC/MS), supercritical fluid chromatography, ion chromatography (IC/MS), capillary electrophoresis (CE/MS), gel electrophoresis, ion mobility, and pyrolysis.

3. The method of claim 1, where the mass spectrometer is one of a sector mass spectrometer, quadrupole mass spectrometer, Time-of-Flight (TOF) mass spectrometer, Orbitrap mass spectrometer, and Fourier-transform ion cyclotron resonance (FT ICR) mass spectrometer.

4. The method of claim 1, where the raw profile mode mass spectral data is calibrated with a known set of standard ions for at least one of mass accuracy and spectral accuracy.

5. The method of claim 1, where the time profile for a compound of interest is the measured actual time profile.

6. The method of claim 1, where the actual separation time profile has been calibrated into a known target profile.

7. The method of claim 6, where the time profile calibration is accomplished through a set of well separated time profiles at a plurality of time points.

8. The method of claim 7, where the well separated time profiles are taken from within the same run as the compounds of interest.

9. The method of claim 7, where the well separated time profiles are taken from another run containing a set of known standards.

10. The method of claim 1, wherein the detection of the presence of possible compounds of interest includes a regression using one of actual or target time profiles with t-statistics indicating the likelihood or confidence for the peaks or compounds detected.

11. The method of claim 1, wherein mass spectral raw profile mode data in the relevant time window are analyzed through principal component analysis to determine the statistically significant number of compounds present.

12. The method of claim 11, where the principal component analysis can be performed through one of singular value decomposition and Nonlinear Iterative Partial Least Squares (NIPALS) algorithm.

13. The method of claim 1, where the separation time profiles for the detected compounds of interest are obtained through a regression analysis with one of actual or target time profiles located at respective time locations which are determined in the process.

14. The method of claim 13, where the time locations of various separation profiles are found in an optimization process through the use of initial values and an iterative algorithm to improve on the initial values.

15. The method of claim 14, where the iterative optimization algorithm includes Simplex optimization.

16. The method of claim 1, where the pure component mass spectra are computed from the measured mass spectra and the obtained separation time profiles.

17. The method of claim 16, where the computation is performed as a regression analysis between the measured mass spectra and the obtained separation time profiles.

18. The method of claim 17, where the regression analysis is a multiple linear regression through the use of one of matrix computation, matrix inversion, singular value decomposition, principal component analysis, and partial least squares.

19. The method of claim 1, where a quantitative analysis is performed by the use one of obtained separation time profiles, computed pure component mass spectra, and information related to their respective scales or intensities.

20. The method of claim 19, where the quantitative analysis is performed through the use of standards with known concentrations.

21. The method of claim 19, where the quantitative analysis is performed through the use of relative intensities of one of time profiles and pure mass spectra among the relevant compounds detected.

22. The method of claim 1, where a qualitative analysis is performed by one of searching the computed pure component mass spectra against a known compound spectral library, comparing the measured separation time profile location to separation time locations of known compounds in a library, computing a mass accuracy for a candidate ion, computing a spectral accuracy for a candidate ion.

23. The method of claim 22, where a library search score is combined with a matching quality from at least one of separation time profile location, mass accuracy, and spectral accuracy into an overall score to indicate a likelihood of correct identification.

24. The method of claim 22, where the candidate ion is one of the molecular ion and fragment ion observed in the acquired mass spectral data and known as belonging to a compound contained in a library.

25. The method of claim 22, where the candidate ion is one of the molecular ion and fragment ion observed in the acquired mass spectral data and comes from an unknown compound.

26. The method of claim 1, where possible compounds are tentatively identified by comparing the measured separation time profile locations, their associated error bounds, the time profile locations of known compounds, and their associated error bounds.

27. The method of claim 26, where a regression analysis between a library spectra of tentatively identified compounds and acquired mass spectra in a relevant time window is performed to obtain estimated relative concentrations of respective tentatively identified compounds and corresponding statistical measures indicating their significance.

28. The method of claim 27, where the statistical measures are the t-values of the estimated relative concentrations.

29. The method of claim 1, where the acquired raw profile mode mass spectral data are corrected for mass spectral skew arising from the finite scan time between one end of mass spectrum to another during active time-based separation of compounds.

30. The method of claim 29, where the skew correction is accomplished through interpolation where the mass spectrum for each scan has been interpolated to correspond to the same point in time during the separation process.

31. The method of claim 1, where the separation time profile is the chromatogram from liquid or gas chromatographic separation and the separation time profile location is the corresponding retention time.

32. The method of claim 1, where the retention time is converted into retention index to indicate the time location when a compound is expected during separation.

33. The method of claim 1, where the computed pure mass spectra are processed into centroids for qualitative identification or quantitative analysis.

34. A mass spectrometer operating in accordance with the method of claim 1.

35. For use with a computer associated with a mass spectrometer, a computer readable medium having computer readable program instructions readable by the computer for causing the mass spectrometer to operate in accordance with the method of claim 1.

36. A method for the analysis of a sample through separation over time combined with detection by a mass spectrometer, comprising the steps of:
  a. obtaining mass spectral data in a raw profile mode of a known sample and an unknown sample;
  b. combining mass spectral scans for a sample into a single mass spectrum through the use of one of summing and averaging across a separation time window;
  c. performing multivariate statistical analysis of the combined mass spectral data and computing a distance measure between at least one known sample and one unknown sample; and
  d. using the distance measure as an indication for an unknown sample as to whether the unknown sample belongs to a known sample group or is indicative of a different sample group.

37. The method of claim 36, where the technique for separation is one of gas chromatography (GC/MS), liquid chromatography (LC/MS), supercritical fluid chromatography, ion chromatography (IC/MS), capillary electrophoresis (CE/MS), gel electrophoresis, ion mobility, and pyrolysis.

38. The method of claim 36, where the mass spectrometer is one of a sector mass spectrometer, quadrupole mass spectrometer, Time-of-Flight (TOF) mass spectrometer, Orbitrap mass spectrometer, and Fourier-transform ion cyclotron resonance (FT ICR) mass spectrometer.

39. The method of claim 36, where the raw profile mode mass spectral data is calibrated with a known set of standard ions for at least one of mass accuracy and spectral accuracy.

40. The method of claim 36, where a profile mode mass spectral data acquired of a known sample is placed into a library as a collection of known samples for future analysis.

41. The method of claim 36, wherein a sample is acquired and analyzed more than once to establish the statistical threshold for the reliable differentiation of one sample from another.

42. A mass spectrometer operating in accordance with the method of claim 36.

43. For use with a computer associated with a mass spectrometer, a computer readable medium having computer readable program instructions readable by the computer for causing the mass spectrometer to operate in accordance with the method of claim 36.

\* \* \* \* \*